United States Patent [19]

Malkamäki

[11] Patent Number: 5,038,790
[45] Date of Patent: Aug. 13, 1991

[54] METHOD AND APPARATUS FOR CONTROLLING THE CUFF PRESSURE IN A SPHYGMOMANOMETER

[75] Inventor: Lauri J. Malkamäki, Vantaa, Finland

[73] Assignee: Instrumentarium Corporation, Finland

[21] Appl. No.: 357,374

[22] Filed: May 25, 1989

[30] Foreign Application Priority Data

May 20, 1988 [FI] Finland .................................. 882414

[51] Int. Cl.$^5$ .............................................. A61B 5/02
[52] U.S. Cl. ..................................... 128/677; 128/685
[58] Field of Search ......................... 128/672, 677–686

[56] References Cited

U.S. PATENT DOCUMENTS

| 4,116,230 | 9/1978 | Gorelick | 128/2.05 M |
|---|---|---|---|
| 4,378,807 | 4/1983 | Peterson et al. | 128/677 |
| 4,501,280 | 2/1985 | Hood, Jr. | 128/677 |
| 4,567,899 | 2/1986 | Kamens et al. | 128/685 X |
| 4,768,518 | 9/1988 | Peltonen | 128/677 |
| 4,800,892 | 1/1989 | Perry et al. | 128/677 |

FOREIGN PATENT DOCUMENTS

WO84/00290 2/1984 PCT Int'l. Appl. .
WO87/02232 4/1987 PCT Int'l Appl. .
2087238 5/1982 United Kingdom .

Primary Examiner—Lee S. Cohen
Assistant Examiner—J. P. Lacyk
Attorney, Agent, or Firm—Andrus, Sceales, Starke & Sawall

[57] ABSTRACT

The invention relates to a method and an apparatus for controlling the cuff pressure in a sphygmomanometer. The pressure control mechanism for a cuff (3) consists of one or a plurality of valves (4) whose operation is controlled by a control element (5) in a manner that the pulse frequency of valve (4) or valves (4) exceeds that of the heart. By using a pulse-controlled high-speed so-called on-off valve it is possible to effect the cuff pressure drop in a completely linear fashion by opening and closing the valve at a necessary frequency and by adjusting the durations of the on- and off-periods of said valve or valves.

26 Claims, 1 Drawing Sheet

METHOD AND APPARATUS FOR CONTROLLING THE CUFF PRESSURE IN A SPHYGMOMANOMETER

BACKGROUND OF THE INVENTION

The present invention relates to a method and apparatus for controlling the cuff pressure in a non-invasive sphygmomanometer. The cuff pressure control mechanism comprises one or a plurality of valves whose operation ion is controlled by means of one or a plurality of control elements in a manner that the valve or valves have an operating frequency which is above the heart beat rate of the heart.

The blood pressure is generally tested by pumping air into a cuff which is wrapped e.g. around the arm of a patient. When the cuff pressure is sufficiently high to stop arterial blood circulation, the reduction of pressure is initiated. As the cuff pressure drops so-called Korotkoff sounds are listened for. As the sound becomes audible, the reading of systolic pressure is obtained. As the pressure drop is continued, the Korotkoff sounds gradually cease altogether. The reading of diastolic pressure is obtained at the moment the sounds cease to be audible.

The Finnish Patent application No. 853781, corresponding to U.S. Pat. No. 4,768,518, described an apparatus used in automatic blood pressure testing, comprising a cuff, a pump and at least two magnetic valves provided with a throttle element, as well as a microprocessor. The throttle element consists of a thin tube whose length has an effect on the pressure reduction rate. It is customary to employ a plurality of throttle elements in a single apparatus, each throttle element being fitted with a tube of different length. Each throttle element is controlled by its own magnetic valve. The magnetic valves are controlled by means of a microprocessor which opens a given magnetic valve depending on which magnetic valve has behind it a throttle element that is best suitable for maintaining a linear cuff air pressure reduction rate at a given moment. If necessary, several magnetic valves can also be opened at the same time. A problem in this type of apparatus is that it requires a plurality of bulky components consisting of a magnetic valve and a throttle element and, nevertheless, it is not possible to obtain a linear rate of the cuff pressure reduction. In addition, opening an of valves leads to disturbances in testing. Also, a pressure drop profile cannot be freely adjusted.

The cuff pressure reduction can also be controlled by using a stepping motor driven needle valve. In order to maintain a uniform pressure drop, the valve must be adjusted during testing. This type of system requires expensive equipment as the manufacturing process is quite complicated. Another problem in this apparatus is malfunctions caused by dust.

SUMMARY OF THE PRESENT INVENTION

An object of this invention is to eliminate the above problems. Thus, an object of the invention is to provide a simple, inexpensive and compact solution. Another object is to achieve a linear cuff pressure drop.

The characterizing features for an apparatus of the invention are set forth in the annexed claims.

The invention is based on a remarkable discovery that by using a pulse-controlled high-speed valve the cuff pressure drop can be effected in a completely linear fashion. The valve control is effected on the basis of a measured reading received from a cuff pressure measuring element.

The processing of a measured reading and the valve control effected on the basis thereof requires,,some special control means which can be e.g. an analog or digital circuit. A particularly noteworthy digital circuit is a microprocessor. Microprocessors compatible with this apparatus are commercially available. The microprocessor should be provided with a pulse-width modulated output.

In an analog controlled system, a signal coming from a pressure sensor is compared in a buffer amplifier with an analog uniformly falling control signal. The output of a buffer amplifier controls the pulse valve by means of pulse-width modulation.

The most important feature is, however, that, on the basis of a measured reading received from the pressure measuring element, the control means for effecting the valve control is capable of controlling the valve opening and closing to occur with a sufficient frequency and for periods of time of determined duration. One such control means is sufficient but of course more than one can be used.

By adjusting the width of a pulse transmitted by an analog or digital circuit it is possible to achieve a stepless regulation of the amount of a gas or liquid flowing through the valve per unit time. In practice, this is performed by having the valve open for a certain determined period of time, whereby a gas or liquid contained in the cuff tends to flow out of it, followed by having the valve closed for a determined period. The duration of these successive open-closed cycles is automatically controlled by these circuits according to measured readings provided by the pressure measuring means or element. Thus, the pressure drop profile is freely adjustable. The application of a sufficiently high pulse frequency serves to avoid the disturbing effect on blood pressure testing caused by pressure shocks. The optimum pulse frequency is 35-60 Hz. However, the pulse frequency must be higher than the heart so as not to disturb the actual blood pressure testing process In fact, there is no actual upper limit to the possible pulse frequency.

Thus, an apparatus of the invention can operate in a manner that either the valve has a constant pulse frequency but a varying pulse width, as mentioned above, or the valve has a varying pulse frequency but a constant pulse width. The apparatus can also be adapted to operate in a manner that both pulse frequency and pulse width of the valve can be varied during a blood pressure testing period. Naturally, both pulse frequency and pulse width of the valve can be maintained constant, but a problem then is that the cuff pressure drop does not occur in a linear fashion. In this latter case, an attempt to correct the linearity can be made by varying pulse frequency, pulse width or both stepwise at properly selected intervals during the same testing cycle. The first-mentioned alternative must be considered preferable.

In an apparatus of this invention, a single valve is sufficient. Of course, more than one valve can be used in parallel. One advantage gained by the use of several valves can be considered to be a prolonged service life for the valves. On the other hand, the space required by several valves can be considered a drawback.

Suitable valves include so-called on-off valves which, accordingly, are either in an open or closed position.

This type of valves includes e.g. a solenoid valve, a piezoelectric valve and a magnetostrictive valve. However, a solenoid valve is perhaps the best choice for this type of blood pressure tester. A solenoid valve is highly durable. The durability of a piezoelectric valve would be even better but its drawback is a rather high operating voltage.

The valve can be placed at many different locations in a blood pressure testing apparatus. A preferred position is in connection with a tube running from pump to cuff. Other possible locations are e.g. the cuff itself, a separate tube issuing from the cuff, a tube running from cuff to pressure sensor, or perhaps the pump or a separate tube issuing from the pump. However, location of the valve is not of critical importance in terms of this invention.

An apparatus of this invention does not require a throttle element in connection with the valve, since the valve alone is capable of controlling a linear drop for the cuff pressure. Hence, this is simply effected by opening and closing the valve as often as necessary and by adjusting the durations of on- and off-periods for the valve.

Due to the pneumatic attenuation of tubes, connectors and cuff, no major shock-like changes are found in the cuff pressure even though the valve operates on the on-off technique. The cuff pressure drop is indeed linear.

A cuff pressure drop system is by no means dependent on the size of a cuff. Thus, cuffs of varying sizes can be used without problems.

BRIEF DESCRIPTION OF THE DRAWING

The invention will now be described in more detail with reference made to the accompanying drawing, in which the drawing shows a general plan for an apparatus of the invention.

DETAILED DESCRIPTION OF THE PREFERRED EMBODIMENT

Figure 1:
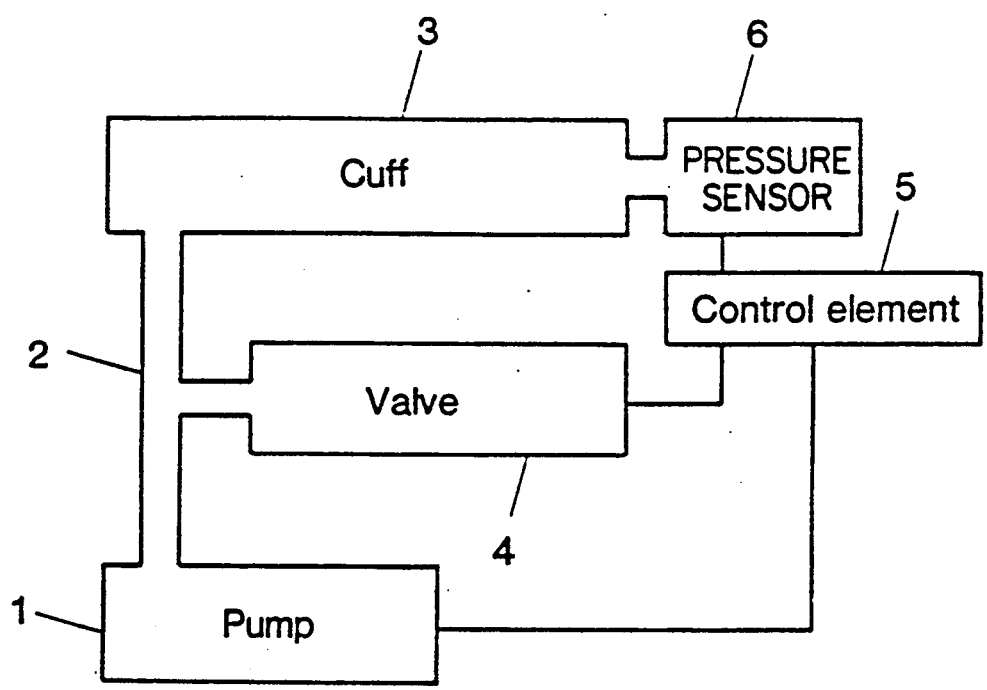

The apparatus shown in the drawing includes any conventional pump 1 with a tube 2 leading to a cuff 3. The tube 2 is fitted with a valve 4 for the reduction of pressure. The valve is controlled by a control element 5 which in turn operates on the basis of a measured reading received from a pressure sensing member 6 in connection with the cuff. The same control element 5 is also capable of controlling the operation of pump 1.

Pump 1 is used to pump a sufficiently high pressure in cuff 3. As pressure is reduced, a pulse-controlled high-speed valve 4 opens and closes repeatedly several times during a single blood pressure testing cycle. By using the valve-regulating control element 5, such as an analog or digital circuit, it is possible to regulate the pressure drop of cuff 3 in a completely linear manner. The pressure drop rate can also be freely controlled by means of said control element 5 which regulates valve 4. The operation of valve 4 can be controlled by means of control element 5 primarily in four different ways:

(A) The pulse frequency of valve 4 is maintained constant but the pulse width is varied. When the pressure in cuff 3 is high, said valve 4 is open for a short period per one on-off cycle. When the pressure is lower than the initial pressure, for example, said valve 4 is open for a longer period per one on-off cycle, since the amount of outflowing air per unit time is smaller than in the case when the pressure in cuff 3 is higher. The frequency of the valve opening times remains unchanged.

(B) The pulse width of valve 4 is maintained constant but the pulse frequency of valve 4 is varied. In this case, the opening period of valve 4 in successive on-off cycles remains the same throughout a blood pressure testing process. Instead valve 4 is opened in a certain unit time more frequently the lower the pressure drops cuff 3.

(C) Both pulse width and pulse frequency of valve 4 are varied. In this case, both the opening period of valve 4 in successive on-off cycles and frequency of the opening times of valve 4 can be varied.

(D) Both pulse width and pulse frequency of valve 4 remain constant either for the entire period required by a blood pressure testing process or just for part of the period required by a testing process. Thus, in the former case, the opening period of valve 4 in successive on-off cycles remains constant and the same applies to the frequency of the opening times of valve 4. In the latter case, the opening period of valve 4 in successive on-off cycles remains constant for a certain period of time as also does the frequency of the opening times of valve 4 but the opening period and the frequency of the opening times of a valve or both of these can be varied at certain intervals during one and the same testing cycle.

I claim:

1. Apparatus for altering the pressure exerted by the fluid in a cuff (3) of a sphygmomanometer applied to a patient from a first pressure level to a second pressure level, the patient having a heart beat rate, said apparatus comprising:
    at least one valve (4) suitable for being coupled in fluid communication to the cuff for controlling the amount of fluid contained in the cuff by means of opening and closing the valve; and
    at least one control element (5) coupled to said valve for periodically, successively, opening and closing said at least one valve at a frequency of 35Hz or greater, each opening and closing of the valve altering the cuff pressure by a small increment in the same direction toward a selected one of the first or second pressure levels, the periodic succession of openings and closings of said at least one valve at said frequency causing the cuff pressure to change from the first pressure level to the second pressure level.

2. An apparatus as set forth in claim 1 wherein said at least one valve is an on-off valve.

3. An apparatus as set forth in claim 1 wherein said at least one valve is a solenoid valve, a piezoelectric valve, or a magnetostrictive valve.

4. An apparatus as set forth in claim 1 in which a single valve is employed.

5. An apparatus as set forth in claim 1 further including a pressure sensor (6) suitable for being coupled to the cuff for sensing the pressure therein, said pressure sensor being coupled to said control element for controlling the operation of said at least one valve responsive to the pressure sensed in the cuff.

6. An apparatus as set forth in claim 1 wherein said at least one valve is suitable for being coupled to the cuff.

7. An apparatus as set forth in claim 1 wherein the sphygmomanometer has a fluid pressure source (1) connected by a tube (2) to the cuff and wherein at least on said valve is suitable for being coupled to the tube.

8. An apparatus as set forth in claim 1 wherein the cuff has a fluid communication means operatively associated therewith and wherein said at least one valve is suitable for being coupled to the fluid communication means.

9. An apparatus as set forth in claim 5 wherein said at least one valve is interposed between said pressure sensor and the cuff.

10. An apparatus as set forth in claim 1 wherein the sphygmomanometer has a fluid pressure source coupled to the cuff and wherein said at least one valve is operatively associated with the fluid pressure source.

11. An apparatus as set forth in claim 1 wherein the apparatus includes a fluid pressure source (1) suitable for being coupled to the cuff and wherein said at least one control element is connected to said fluid pressure source.

12. An apparatus as set forth in claim 1 wherein said at least one control element is further defined as periodically opening and closing said at least one valve at a frequency of 35–60 Hz.

13. An apparatus as set forth in claim 1 wherein said at least one control element is further defined as comprising one of an analog or digital control element.

14. An apparatus as set forth in claim 1 wherein said at least one control element is further defined as comprising a microprocessor.

15. An apparatus as set forth in claim 1 wherein said at least one control element is further defined as periodically opening and closing said at least one valve in a pulse width modulated manner.

16. An apparatus as set forth in claim 14 wherein said microprocessor is further defined as periodically opening and closing said at least one valve in a pulse width modulated manner.

17. Apparatus for reducing the pressure exerted by the fluid in a cuff (3) of a sphygmomanometer applied to a patient, the patient having a heart beat rate, said apparatus comprising:
a fluid pressure source (1) suitable for being coupled to the cuff for supplying pressurizing fluid thereto;
at least one valve (4) suitable for being coupled in fluid communication to the cuff for discharging fluid contained in the cuff by means of opening and closing the valve;
a pressure sensor (6) suitable for being coupled to the cuff for sensing the pressure in the cuff; and
at least one control element (5) coupled to said pressure sensor and to said at least one valve, said at least one control element periodically, successively, opening and closing said valve at a frequency of 35 Hz or greater responsive to the pressure sensed in the cuff, each opening and closing of the valve reducing the pressure in the cuff by a small increment so that the cuff pressure is reduced in a desired manner with respect to time, said fluid pressure source being connected to said at least one control element for being controlled thereby.

18. A method for altering the pressure exerted by the fluid in a cuff (3) of a sphygmomanometer applied to a patient from a first pressure to a second pressure level, the patient having a heart beat rate, said method comprising the step of:
repetitiously opening and closing a valve controlling the amount of fluid contained in the cuff at a frequency of 35 Hz or greater, each opening and closing of the valve altering the cuff pressure by a small increment toward a selected one of the first or second pressure levels, the repetitious openings and closings of the valve causing the cuff pressure to change from the first pressure level to the second pressure level.

19. A method as set forth in claim 18 further defined in that as the pressure in the cuff is altered, the frequency of repetitiously opening and closing the valve is maintained constant while the period during which the valve is open in each cycle of repetition is varied.

20. A method as set forth in claim 18 further defined in that as the pressure in the cuff is altered, the frequency of repetitiously opening and closing the valve is varied while the period during which the valve is open in each cycle of repetition is maintained constant.

21. A method as set forth in claim 18 further defined in that as the pressure in the cuff is altered, the frequency of repetitiously opening and closing the valve and the period during which the valve is open in each cycle of repetition are varied.

22. A method as set forth in claim 18 further defined in that as the pressure in the cuff is altered, the frequency of repetitiously opening and closing the valve and the period during which the valve is open are maintained constant for at least a portion of the time during which the pressure is being altered.

23. A method as set forth in claim 22 further defined in that the frequency of repetitiously opening and closing the valve and the period during which the valve is open are maintained constant for the entire time during which the pressure is being altered.

24. A method as set forth in claim 22 further defined in that the frequency of repetitiously opening and closing the valve and the period during which the valve is open are changed at intervals in the time during which the pressure is being altered but are maintained constant in the periods between the intervals.

25. The method as set forth in claim 18 further defined as including the step of sensing the pressure in the cuff and controlling the repetitious opening and closing of the valve in accordance therewith.

26. The method as set forth in claim 18 further defined as repetitiously opening and closing the valve at a frequency of 35–60 Hz.

* * * * *